(12) United States Patent
Morse et al.

(10) Patent No.: US 7,552,621 B2
(45) Date of Patent: Jun. 30, 2009

(54) METHOD AND APPARATUS FOR V-BANK FILTER BED SCANNING

(75) Inventors: Thomas C. Morse, Greenville, NC (US); Mark Huza, Columbia, MD (US)

(73) Assignee: Camfil Farr, Inc., Riverdale, NJ (US)

( * ) Notice: Subject to any disclaimer, the term of this patent is extended or adjusted under 35 U.S.C. 154(b) by 0 days.

(21) Appl. No.: 11/954,275

(22) Filed: Dec. 12, 2007

(65) Prior Publication Data
US 2008/0087074 A1    Apr. 17, 2008

Related U.S. Application Data

(62) Division of application No. 11/552,409, filed on Oct. 24, 2006, now Pat. No. 7,334,490.

(60) Provisional application No. 60/729,643, filed on Oct. 24, 2005.

(51) Int. Cl.
*G01N 15/08* (2006.01)
(52) U.S. Cl. .......................................................... 73/38
(58) Field of Classification Search ...................... 73/38, 73/865.8, 865.9, 863.54, 863.51, 864.73, 73/864.81
See application file for complete search history.

(56) References Cited

U.S. PATENT DOCUMENTS

| | | |
|---|---|---|
| 3,395,514 A | 8/1968 | Bub |
| 3,473,876 A | 10/1969 | Steinberg |
| 3,490,211 A | 1/1970 | Cartier |
| 4,494,403 A | 1/1985 | Bowers et al. |
| 4,610,706 A | 9/1986 | Nesher |
| 4,686,848 A | 8/1987 | Casselberry et al. |

(Continued)

FOREIGN PATENT DOCUMENTS

DE    19726379    1/1999

(Continued)

OTHER PUBLICATIONS

PCT Search Report and Written Opinion for PCT/US06/41520, copy consists of 13 unnumbered pages, mailed Sep. 13, 2007.

*Primary Examiner*—Hezron Williams
*Assistant Examiner*—Gunnar J Gissel
(74) *Attorney, Agent, or Firm*—Patterson & Sheridan, LLP; Keith P. Taboada (57) ABSTRACT

Embodiments of the invention generally related to a method and apparatus for scanning a v-bank filter. In one embodiment, an apparatus for scanning a v-bank filter includes a hollow body having first and second ends. An outlet, formed at the second end of the body, is adapted for coupling a testing device to an interior volume of the body. A plurality of holes are formed through the body and are fluidly coupled to the interior volume. In another embodiment, a method for scanning a v-bank filter includes inserting a probe having a plurality of sample ports into a filter adjacent a filter pack, and traversing the probe along the filter pack. In yet another embodiment, a method for scanning a v-bank filter includes scanning a slot of a v-bank filter with a probe, and collecting samples of gas passing through the filter an into the probe.

19 Claims, 11 Drawing Sheets

U.S. PATENT DOCUMENTS

| | | |
|---|---|---|
| 5,098,767 A | 3/1992 | Linnersten |
| 5,141,309 A | 8/1992 | Worwag |
| 5,939,617 A | 8/1999 | Lim et al. |
| 6,027,759 A | 2/2000 | Kwok et al. |
| 6,074,450 A | 6/2000 | Raber |
| 6,416,562 B1 * | 7/2002 | Shibuya et al. ............... 55/486 |
| 6,447,566 B1 | 9/2002 | Rivera et al. |
| 6,470,732 B1 | 10/2002 | Breton |
| 6,602,328 B2 | 8/2003 | Doi et al. |
| 6,619,112 B2 | 9/2003 | Juhasz |
| 7,010,960 B1 * | 3/2006 | Grantham ................... 73/40 |
| 7,334,490 B2 | 2/2008 | Morse et al. |
| 2004/0000186 A1 | 1/2004 | Hagg et al. |
| 2004/0146437 A1 | 7/2004 | Arts et al. |
| 2005/0144916 A1 | 7/2005 | Adamek et al. |
| 2005/0188749 A1 | 9/2005 | Custer et al. |
| 2006/0042359 A1 * | 3/2006 | Morse et al. ................. 73/40 |
| 2006/0112757 A1 | 6/2006 | Morse |
| 2006/0272301 A1 * | 12/2006 | Morse et al. ................. 55/439 |
| 2007/0214870 A1 | 9/2007 | Morse et al. |

FOREIGN PATENT DOCUMENTS

| | | |
|---|---|---|
| JP | 04077646 | 3/1992 |

* cited by examiner

SCANNING

FIG. 10

SCANNING
FIG. 11

METHOD AND APPARATUS FOR V-BANK FILTER BED SCANNING

RELATED APPLICATIONS

This application is a divisional of U.S. patent application Ser. No. 11/552,409, filed on Oct. 24, 2006 now U.S. Pat. No. 7,334,490, which claims benefit of U.S. Provisional Patent Application Ser. No. 60/729,643, filed Oct. 24, 2005 by Thomas C. Morse, which are both incorporated by reference in their entireties. Benefit of priority to all of the above-referenced applications is claimed.

BACKGROUND OF THE INVENTION

1. Field of the Invention

The present invention generally relates to a method and apparatus for v-bank filter bed scanning.

2. Description of the Related Art

Many contamination control applications having high airflow requirements utilize v-bank filters over panel filters when laminar flow is not of primary concern. However, conventional manufacturing and validation practices limit testing of v-bank to overall efficiency test due to the inability to accurately leak test (i.e., scan test) the filter media for pin hole leaks. The inability to scan test v-bank filters has been documented in an article published October, 2001 in Cleanrooms Magazine entitled "EN1822: THE STANDARD THAT GREATLY IMPACTED THE EUROPEAN CLEANROOMS MARKET." In the article, the author states that ". . . HEPA/ULPA filters with V-shaped pleat packages cannot be scanned, because the measuring probe cannot be brought close enough to a possible leak in the pleated package."

However, many facilities are forced to utilize deep pleated filter products instead of v-bank filter products because of increasingly stringent validation requirements for contamination control that require scan testing. As deep pleated filters generally do not have the air handling capacity of v-bank filters, more filters may be required for a given application, and more energy may be required to drive gas flows through the filters. Thus, the use of deep pleated filters in applications where v-bank filters could be utilized may realize higher filter and energy usage costs.

Therefore, there is a need for a method and apparatus for scanning v-bank filter beds.

SUMMARY OF THE INVENTION

Embodiments of the invention generally relate to a method and apparatus for scanning a v-bank filter. In one embodiment, an apparatus for scanning a v-bank filter includes a hollow body configured to extend between banks of a v-bank filter during testing. The hollow body has first end and a second end. An outlet is formed at the second end of the body and is adapted for coupling a testing device to an interior volume of the body. A first plurality of holes are formed through the body with are fluidly coupled to the interior volume.

In another embodiment, a method for scanning a v-bank filter is provided. In one embodiment, the method includes inserting a probe having a plurality of sample ports into a filter adjacent to a filter pack, and traversing the probe along the filter pack.

In another embodiment, a method for scanning a v-bank filter includes scanning a slot of a v-bank filter with a probe, and collecting samples of gas passing through the filter an into the probe.

In one embodiment, a probe for scan testing a v-bank filter includes a hollow body having an interior volume, a first end and a second end. The hollow body is configured to extend between the banks of a v-bank filter during testing. An outlet formed at the second end of the body is adapted for coupling an interior volume of the body to a testing device. A first plurality of apertures are formed through the body and fluidly coupled to the interior volume.

In another embodiment, a probe for scan testing a v-bank filter includes an elongated hollow body sealed at a first end and having a port at a second end. A tapered slot is formed through a wall of the body, wherein a wide end of the tapered slot is orientated towards the first end of the body.

In another embodiment, a method for testing a v-bank filter is provided that includes inserting a probe between two banks of filtration media of a v-bank filter, and traversing the probe along the banks, and simultaneously providing samples from each bank individually to a test instrument.

In another embodiment, a method for testing a v-bank filter is provided that includes providing a challenge to a v-bank filter having at least two adjacent banks of filter media arranged in a "v" configuration, scanning a probe across an opening defined between the adjacent banks of filter media, sampling air passing through the banks of filter media and into the probe, determining if a sample is indicative of a leak.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures. It is contemplated that elements and features of one embodiment may be beneficially incorporated in other embodiments without further recitation.

It is to be noted, however, that the appended drawings illustrate only exemplary embodiments of this invention and are therefore not to be considered limiting of its scope, for the invention may admit to other equally effective embodiments.

DETAILED DESCRIPTION

Embodiments of the invention are suitable for scan testing v-bank filters for pin-hole leaks. Although the filter illustrated herein is a FILTRA 2000™ v-bank filter available from Camfil Farr, Inc., it is contemplated that the testing apparatus and method may be utilized to scan test v-bank filters having other configurations. A scan probe developed to facilitate scan testing enables reasonable scan rate (i.e., in the range of about 1-2 inches per second (25.4-50.8 millimeters per second)) for manual scan operations and may further be adapted for use in automatic or semi-automatic scan applications.

Probe Design

The V-bed media pack configuration creates obstacles in the scan test process and probe design, as compared to a conventional box-style media packs, where the face of the entire pack is in a single plane. In conventional box-style filters, the probe generally consists of a tube with an integral transition through which the sample is drawn. The transition is generally square or rectangular. The design of this type of sampling probe is such that the localized velocities across the sampling plane of the probe are equivalent, resulting in uniform airflow across the sampling plane.

In the present invention, a probe allows adjacent media packs to be scanned simultaneously. Although this isn't necessary, it is desirable because it reduces the number of "passes" per filter that an operator has to make with the probe when testing a filter. It is contemplated that the probe may be configured to scan only one media pack in a single pass.

FIGS. 1-8 depict various views of probes suitable for scan testing a v-bank filter. The samples taken during the scan may be utilized for determining the location of pin-hole leaks greater than a predetermined criteria or filter efficiency. Referring first to a probe 100 depicted in FIGS. 1A-B, the probe 100 is generally a tube or other hollow body 102 sealed at a first end 104 and having a port 106 at a second end 108. The shape of the body 102 is configured to allow the first end 104 of the probe 100 to be positioned between adjacent banks of a v-bank filter. The port 106 is generally adapted to coupling to a test instrument, such as a photometer, particle counter or other instrument suitable for leak detection or efficiency measurement. In one embodiment, a length of stainless steel tubing is bent into a configuration that fits into the "V" defined by the filter banks, for example, a "V" or triangle shape. In other embodiment, the tubing may be straight or wedge shaped. A plurality of apertures 110, such as holes or slots, are formed, for example by drilling, along outward facing side of at least one leg of the probe 100. The number, size and spacing of the apertures 110 are selected to allow sampling along the length of the media bank perpendicular to the direction of scan. As such, the length of the probe having the apertures 110 formed therethrough is generally equal to the length of the media bank for which the probe is intended to be used. Thus, the apertures 110 on each leg face in opposite directions. In the embodiment depicted in FIG. 1, each leg of the probe 100 includes a linear arrangement of apertures 110. The interior volume of each leg is fluidly coupled to the port 106 such that samples taken through the apertures 110 may be provided to the test instrument.

The apertures 110 may be of a single, different or a combination of sizes. In one embodiment, the orifice, or plan area of the apertures 110 formed through the probe wall is reduced between holes extending along the length of the probe towards the first end 104 to account for pressure losses due to the sample being drawn from the second end 108 of the probe. In one embodiment, the apertures 110 include at least two groups of holes and/or slots having different orifice sizes. In the embodiment depicted in FIG. 1B, the apertures 110 include a far group of holes 110C at the first end 104 of the probe 100 furthest from the photometer that have a larger diameter (orifice) than the diameter of a near group of holes 110A disposed closest to the second end 108 (and photometer), while a middle group of holes 110B disposed in the midsection of the probe 100 have a diameter somewhere between those the diameters of the apertures 110 closest and farthest from the second end 108. For example, the apertures 110 may include near group of holes 110A having a diameter of about 0.018-0.062 inches (0.45-1.57 mm), middle group of holes 110B having a diameter of about 0.055-0.077 inches (1.40-1.96 mm), and a far group of holes 110C having a diameter of about 0.062-0.093 inches (1.57-2.36 mm). Increasing the hole diameter along the length of the probe 100 results in a more uniform (and representative) sample along the length of the probe. Similar probes could be designed using an aperture 110 configured as a slot that changes in width along the length of the probe (e.g., tapers towards the first end 104), or by using perforated material along the length of the probe that uses larger holes and/or different hole spacing along the length of the probe, in order to achieve the same results.

Figure 1A:
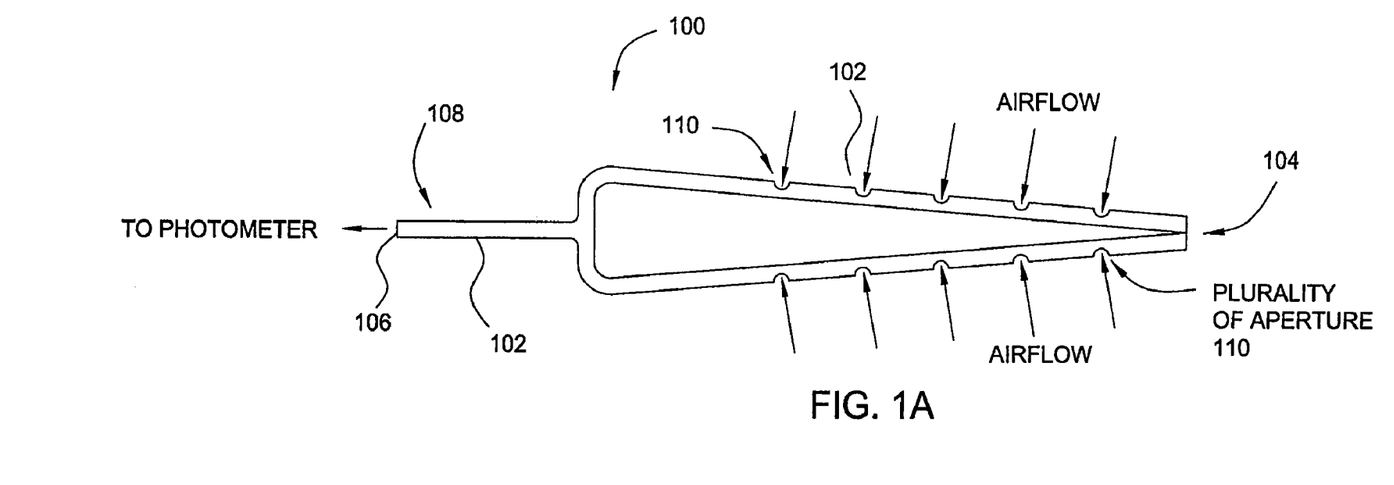
FIGS. 1A-B, 2-3, 4A-B, 5A-B and 6 are various views of different embodiments of a probe suitable for scan testing a v-bank filter.
Figure 1B:
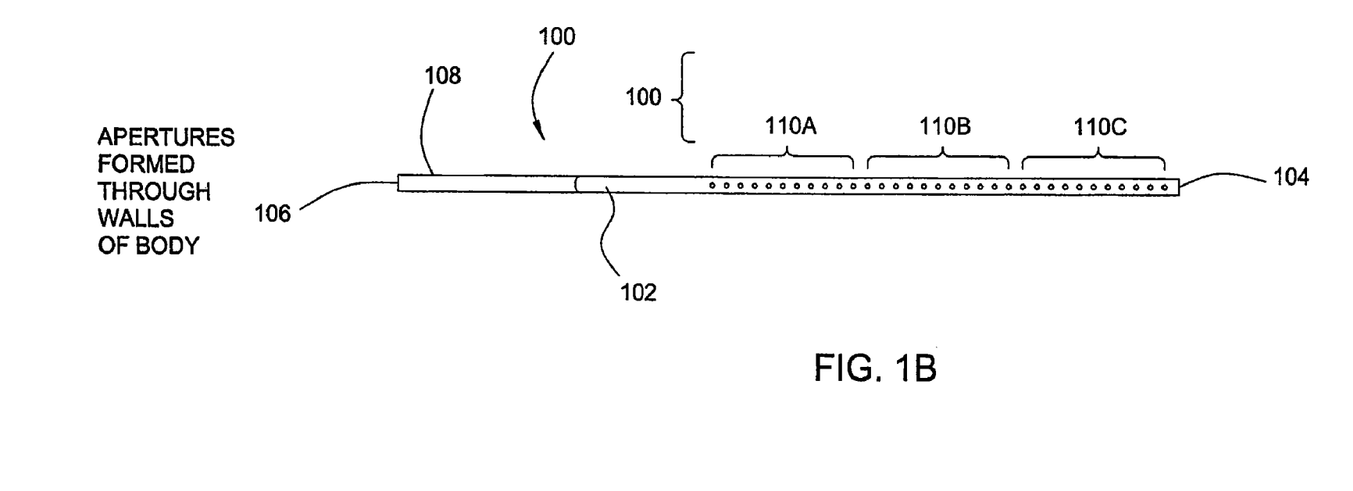
Figure 2:
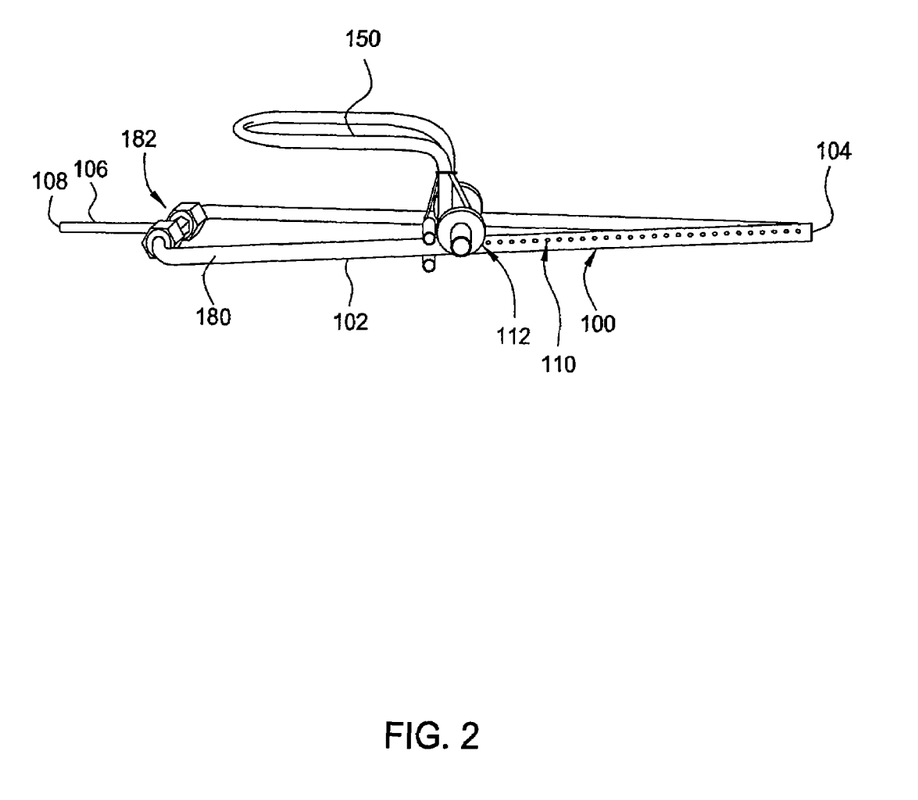
Figure 3:
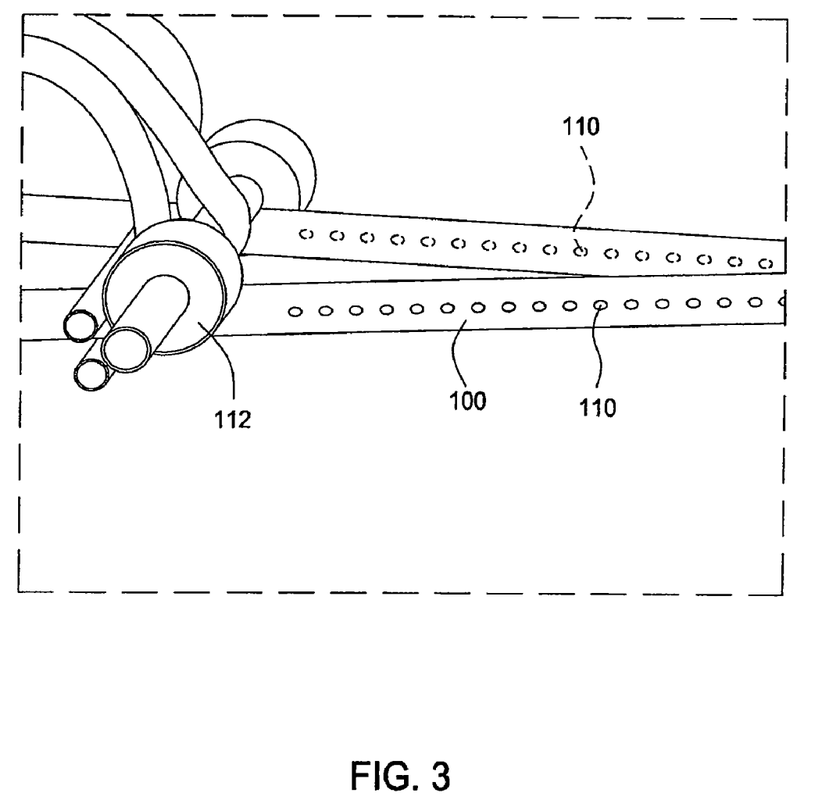

FIGS. 2-3 show the probe 100, including an integral handle 150 and guides 112 to locate the probe 100 in the "V" of the filter during a scan of the filter. These guides 112 allow the probe 100 to maintain at a predefined distance from each media pack by limiting the distance the first end 104 of the probe can be inserted into the filter. The guides 112, such as bars, rods, rollers, bearing, slides, tabs or other fixtures (as seen in FIGS. 2-3 and 8-11), ensure the probe remains reasonably centered between the media packs, thereby eliminating potential damage the media banks by inadvertent contact with the probe 100 during insertion or scanning, and also ensuring that the distance between the probe and the face of the media pack is maintained at the required distance (or range).

Figure 4A:
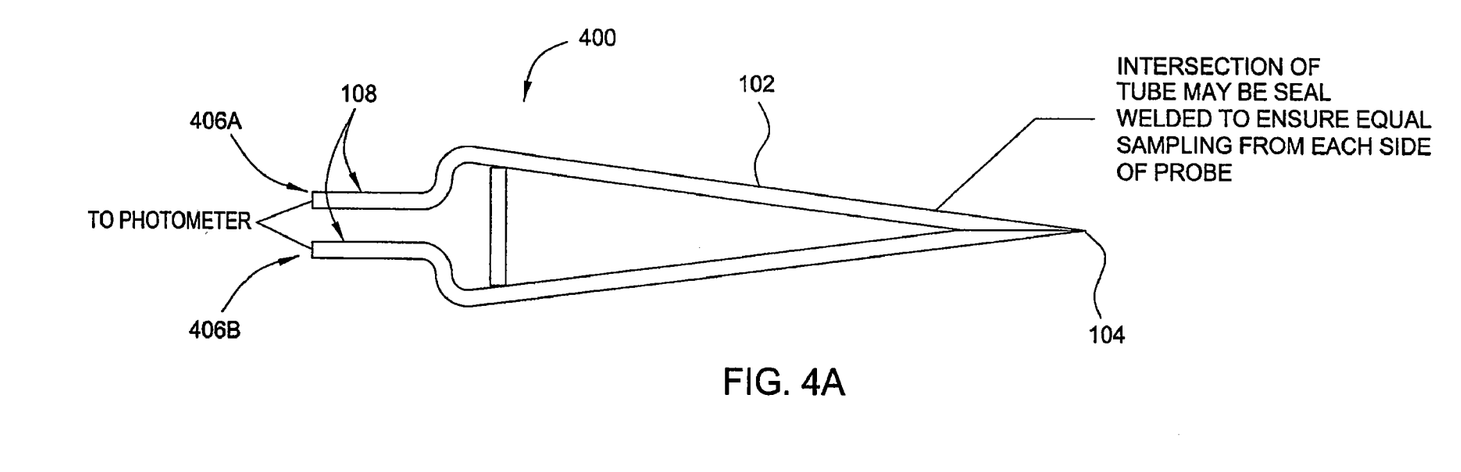
Figure 4B:
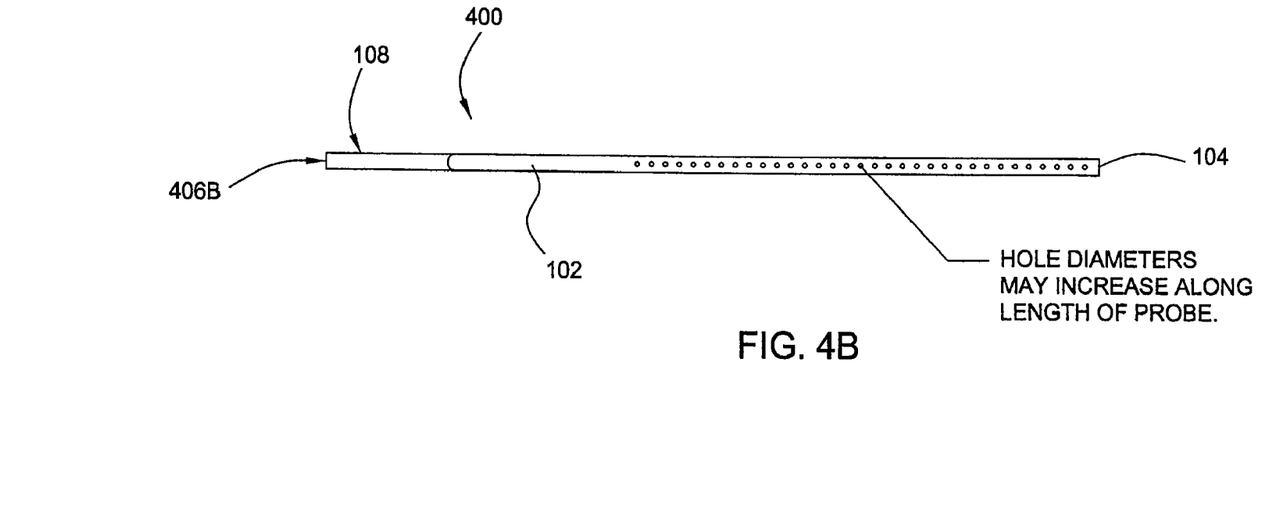
Figure 5A:
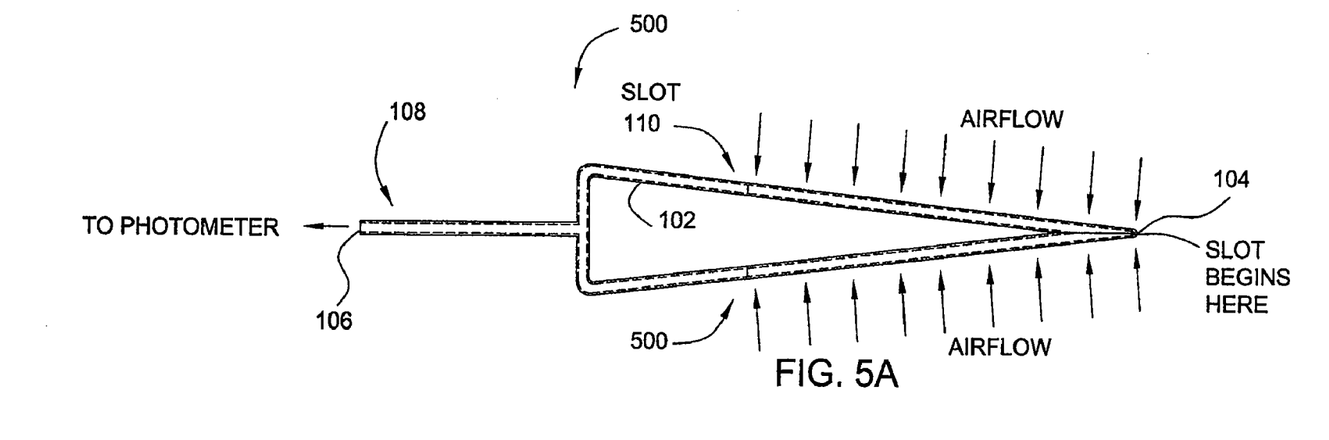
Figure 5B:
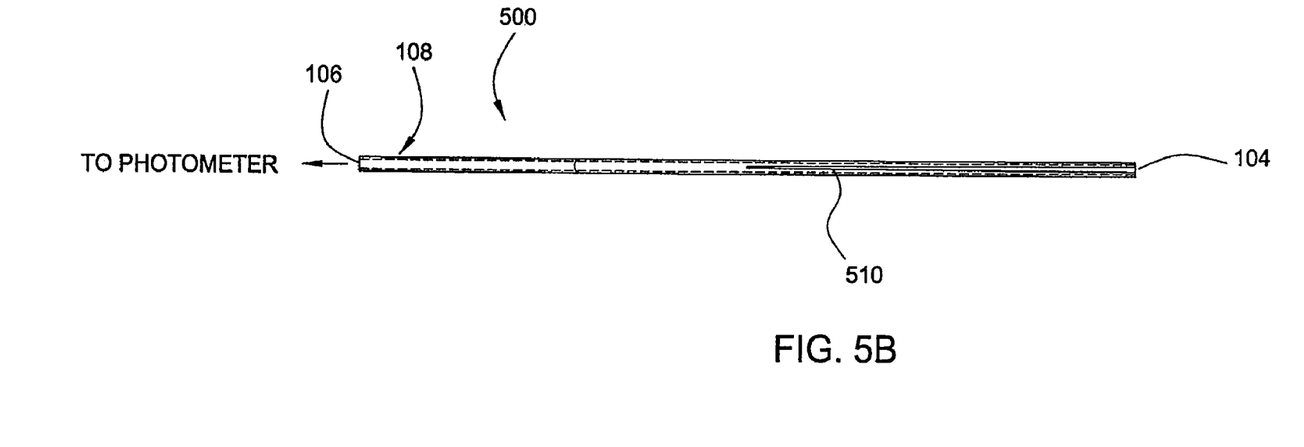
Figure 6:
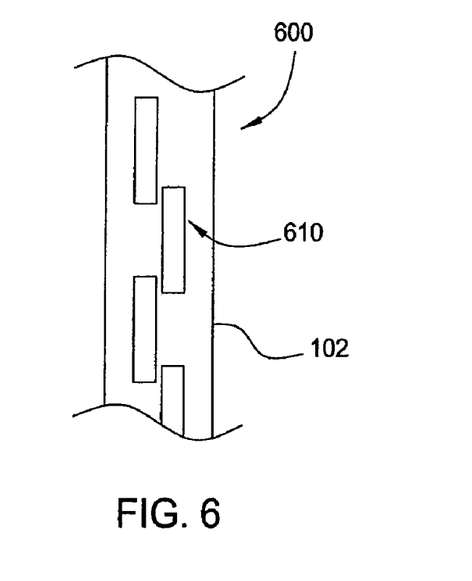

In one embodiment, the probe 100 is fabricated from one or more hollow tubes 180 formed in a V-shape to fit between the pleated media packs. The tubes 180 are coupled near the second end 106 at a tee 182, which extends to the port 108. The apertures 110 of the probe may be designed as a plurality of slots or holes 110A-C (as shown in FIGS. 1A-B, and 2-3), staggered holes 410 (as shown in FIGS. 4A-B), one or more tapered slots 510 (as shown in FIGS. 5A-B), staggered slots or holes 610 (as shown in FIG. 6) or other configurations to allow air sampling within 1" (25.4 mm) of the face of the media pack, which is generally an industry acceptable distance between the media pack and a sampling probe. In embodiments wherein a slot is utilized, the aperture 110 may be a single slot 510 as shown in FIGS. 5A-B, although a plurality of slots may be utilized. The geometry of the probe 100 may be modified in cases where standards or industry practices would require that the probe be located closer to the media pack during scan testing. In embodiments wherein the body 102 is a tube 180, the rounded surface (outer diameter of the tube 180) through which the apertures 110 are formed provides protection against damage to the filter media in the advent that inadvertent contact between the probe and media is made, particularly as compared to conventional rectangular probes having squared corners.

In the embodiment depicted in FIG. 4A-B, a probe 400 includes a body 102 having legs 402, 404 that meet at a first end 104. The legs 402, 404 flare outward from the first end 104 toward a second end 108. Each of the legs 402, 404 includes a separate port 406A, 406B at the second end 108 for coupling each leg separately to a test instrument. Since samples taken through apertures 410 (formed in the legs 402, 404 as described above) are separately sampled, leak detection of the specific bank of filter media proximate an individual leg 402, 404 may be determined.

The apertures 410 may be staggered in size so that the apertures having larger orifice diameters are closer to the first end 104. In one embodiment, the apertures 410 are configured similar to the apertures 110 described with reference to FIG. 1B.

In another embodiment depicted in FIGS. 5A-B, a probe 500 includes a body 102 that may be configured as either the probe 100 or 400 described above. The probe 500 includes a slot 510 formed in the outward facing sides of the legs of the body 102. In one embodiment, the slot 510 may be tapered such that the wide end of the slot 510 is proximate the first end 104 of the body 102.

In another embodiment depicted in FIG. 6, a portion of a probe 600 is shown. The body 102 of the probe 600 that may be configured as either the probe 100 or 400 described above. The probe 600 includes a plurality of staggered apertures 610, shown in FIG. 6 as slots. The apertures 610 formed in the outward facing sides of the body 102 such that a portion of one aperture 610 overlaps the adjacent aperture. In one embodiment, the apertures 610 closer the first end (104) of the body 102 may have more in open area than the apertures 610 is proximate the second end (106).

Figure 7:
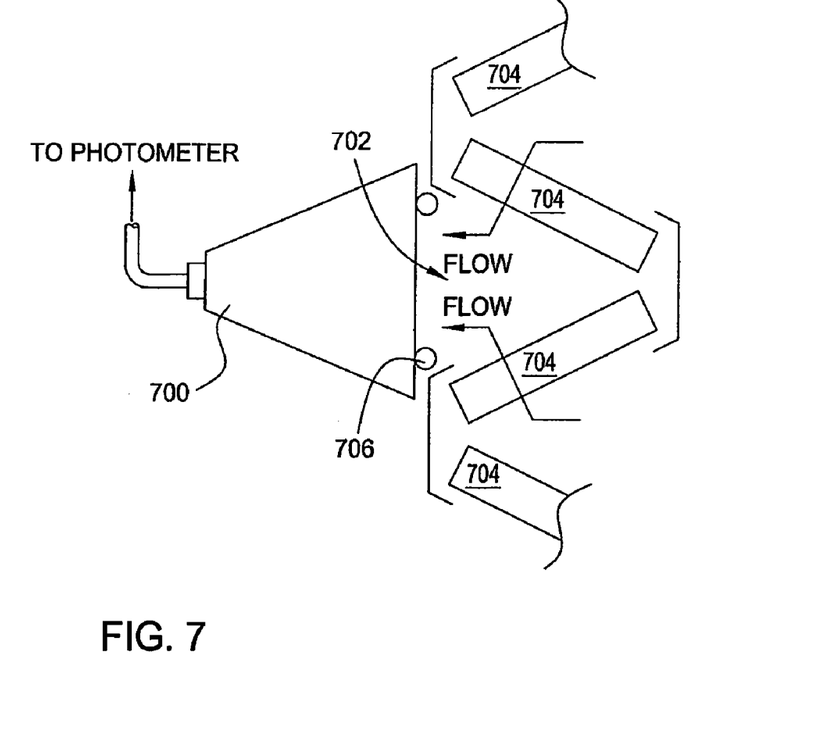
FIG. 7 is another embodiment of a probe suitable for scan testing a v-bank filter.
Figure 8:
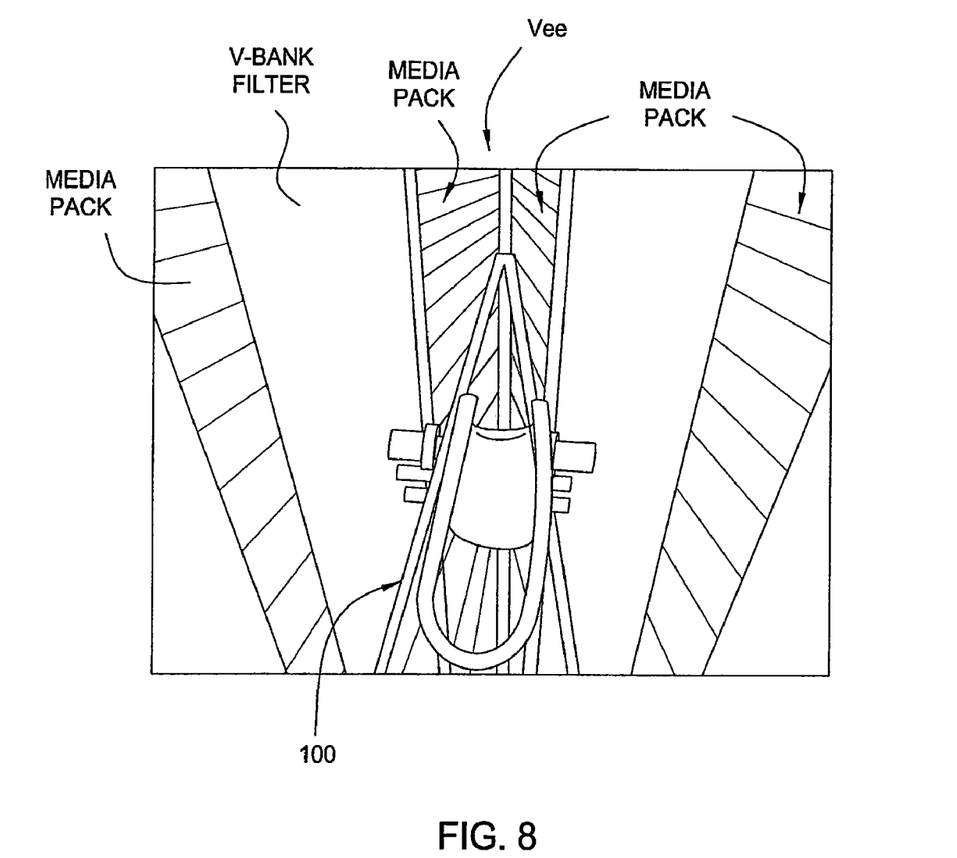
FIGS. 8-11 are images of a probe of the present invention engaged with a v-bank filter to facilitate scan testing.
Figure 9:
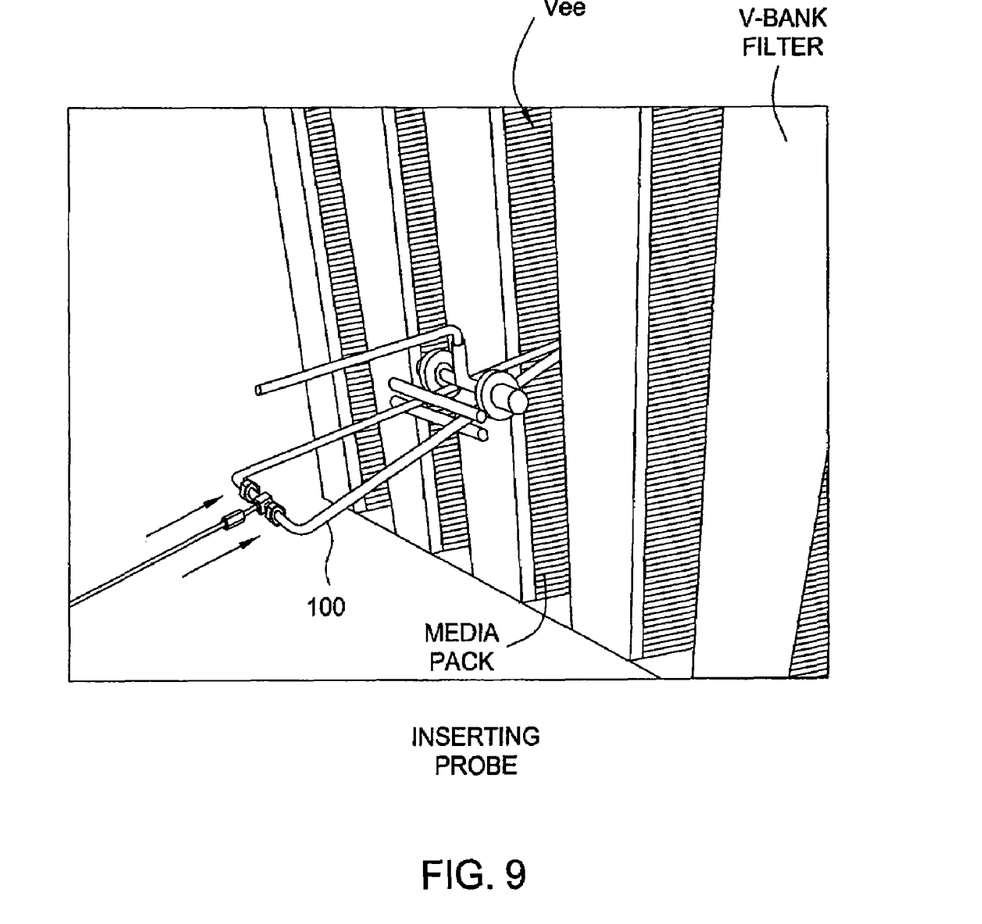
Figure 10:
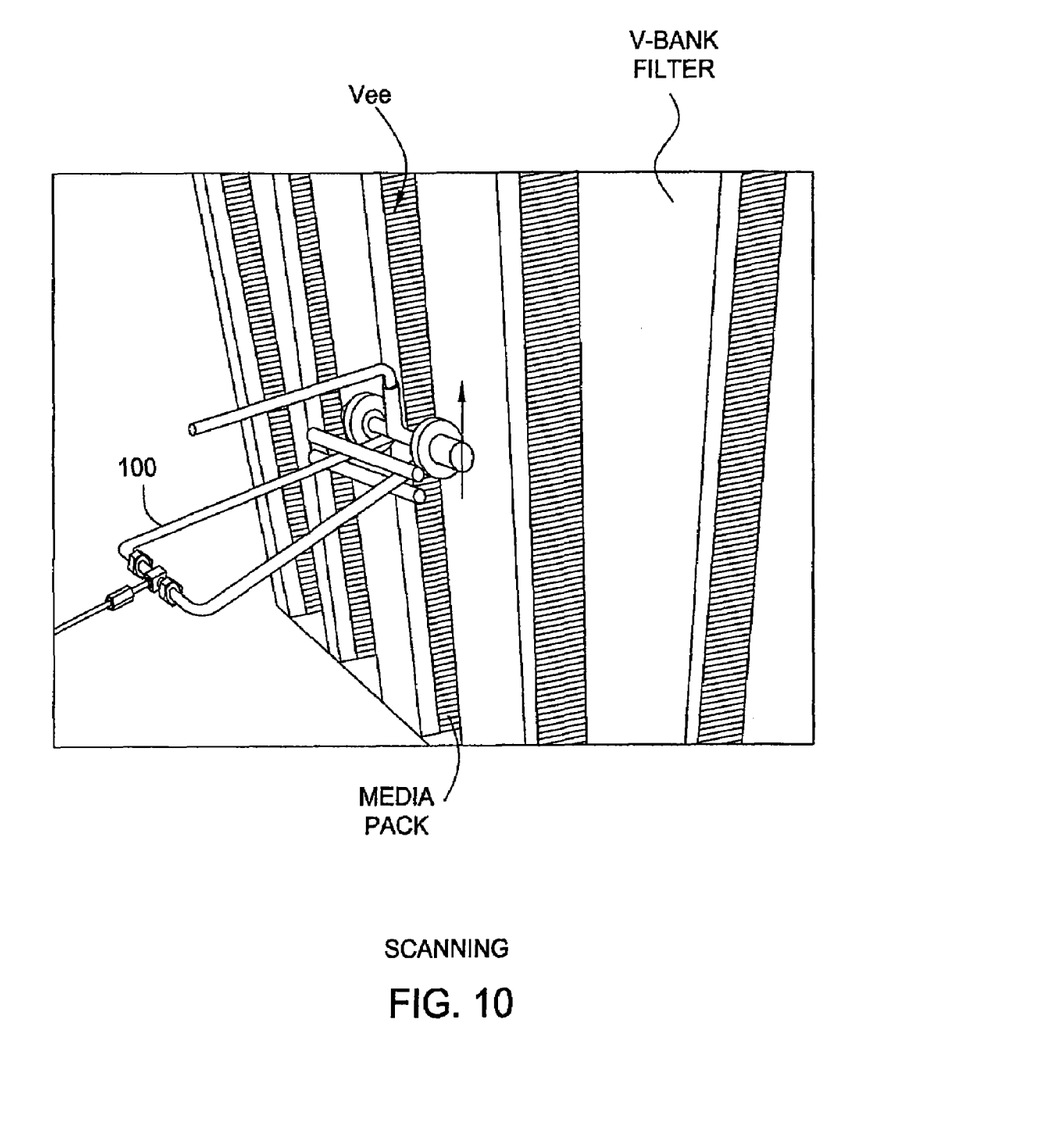
Figure 11:
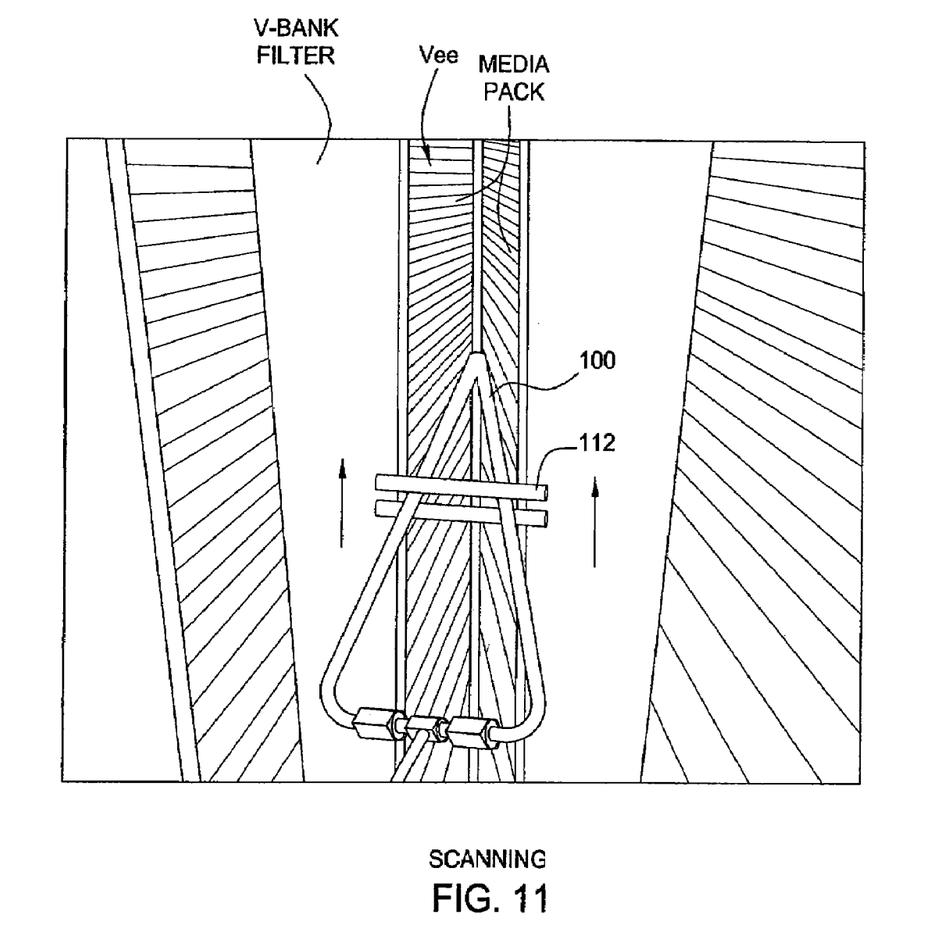

In another embodiment depicted in FIG. 7, the probe 700 has a rectangular shape. The width of the probe is such that it wider than the width of the slot 702 defined at the wide end of the Vee where air exits between the media packs 704 of a v-bank filter. The probe 700 may include one or more guides 706 to align the probe with the slot, such as a rod, roller, bar or other locating features coupled to the open end of the probe 706 as shown in FIG. 7. The probe 700 is placed as near as possible to the slot 702 in order to eliminate potential bypass around the probe. Scan testing is conducted by moving the probe along the slot. This is very similar to scan testing a conventional HEPA filter, except the probe is used to scan the slot instead of the media pack. It is contemplated that scan data may also be utilized to calculate filter efficiency.

Figure 12A:
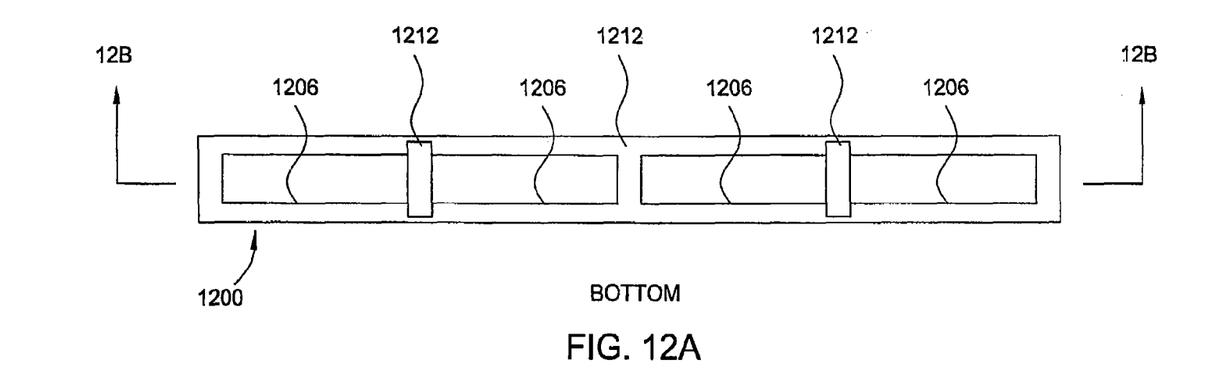
FIGS. 12A-B are another embodiment of a probe suitable for scan testing a v-bank filter.
Figure 12B:
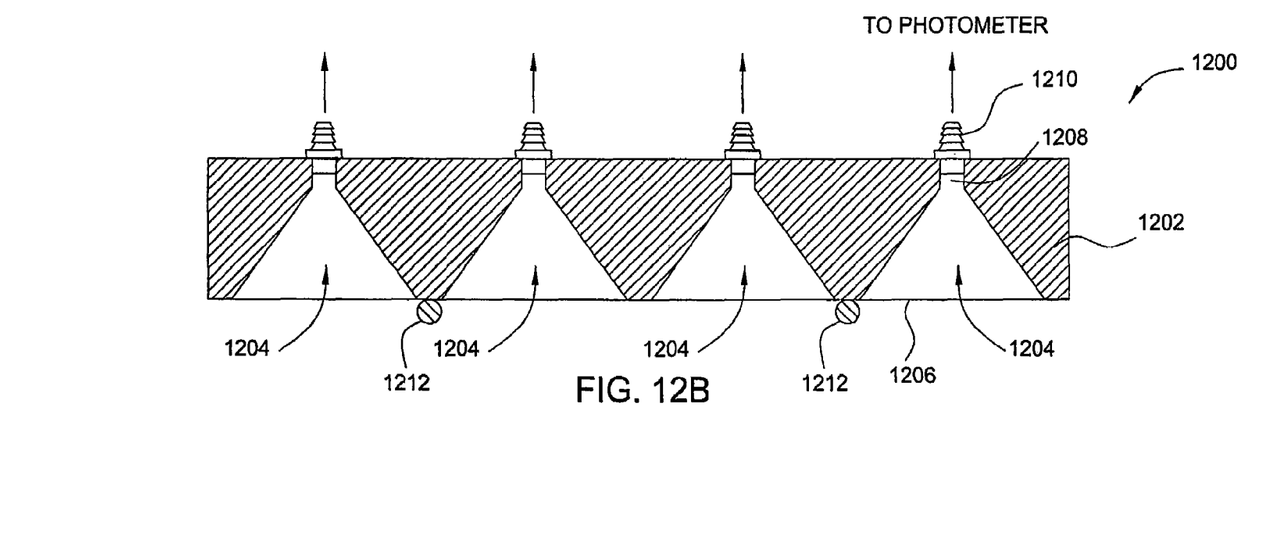

In another embodiment depicted in FIGS. 12A-B, a probe 1200 suitable for scanning a v-bank filter is illustrated. The probe 1200 includes a body 1202 having at least one sample port 1204. In the embodiment depicted in FIGS. 12A-B, four sample ports 1204 are shown.

Each sample port 1204 includes a sample entrance port 1206 and a sample exit port 1208. A fitting 1210 is coupled to the body 1202 at the exit port 1208 to facilitate coupling the port 1204 to a test instruments, such as a photometer or other suitable device.

At least one guide 1212 is provided on the sample entrance port side of the probe 1200. The guide 1212 facilitates alignment of the probe 1200 to the filter as described above. In the embodiment depicted in FIGS. 12A-B, two guides 1212 in the form of bars secured perpendicular to the major axis of the probe 1200 and aligned with the scan direction are provided.

Validation of Probe & Method of Testing V-Bank Filter

The probe of the present invention was demonstrated as being effective for locating leaks. A FILTRA 2000 v-bank filter was utilized during the test. The filter was installed in a test rig and challenged with PAO. The filter was then manually scan tested using the probe described above. The testing is detailed below.

Procedure-Insertion Style Probe

In one embodiment, a probe, such as the probes 100, 400, 500, was utilized to scan test a Filtra 2000™. The probe was used to scan between the banks of filter media within the Vee's from the downstream side of the V-bed filter.

Two holes were intentionally placed in a FILTRA 2000™ v-bank filter using a mechanical pencil with a 0.5 mm diameter lead to create a leak in a known location. "Hole A" was created in the media pack on the downstream side of the filter, on the downstream side of the media pack, at a location approximately 1 inch (25.4 mm) from the vertical extrusion member. "Hole B" was created in the media pack on the upstream side of the filter, on the upstream side of the media pack, at a location very near the vertical extrusion member.

Holes were created in those locations because they represent locations where leaks are generally considered difficult to detect.

The test rig utilized to perform the scan test generally includes a variable frequency drive on the test rig was adjusted until a pressure drop across the air flow station (AFS) was approximately 0.452 inches water gage (w.g.) (0.113 kPa) as measured using an Alnor Micromanometer. This pressure drop across the filter is indicated of approximately 2000 cubic feet per minute (56.6 cubic meters per minute) of flow through the filter.

An ATI TDA-5B thermal generator was used to generate PAO aerosol that was injected into the inlet of the blower. An ATI TDA-2E photometer was used to obtain an upstream sample in the transition immediately upstream of the filter. The blower, aerosol generator and photometer were allowed to warm up for approximately 20 minutes allow steady-state operation to be reached.

The aerosol generator was turned on, and adjusted to obtain between 40-50 micrograms/liter. This range was chosen because various industry standards and recommendations (for examples, IEST and ATI) recommend scanning with an aerosol challenge ranging from 10-100 micrograms/liter. The upstream challenge concentration was measured with the photometer. The filter was scan tested using the prototype probe connected to the photometer and the results were recorded as shown in Table 1 below. The scan was performed by manually inserting the probe into the filter such that the aperture(s) is facing the filter pack to be tested. The probe is then advanced across the pack to test the media for pin-hole leaks. The leak threshold may be set per IEST standards or other test protocol.

Equipment Used
 Test Filter: FILTRA 2000™, available from Camfil Farr, Inc.
  Model Number: FA1570A-01-01-09
  Part Number: 855010095
  Ser. No.: A116084-008
  Label Efficiency: 99.998%
  Label Pressure Drop: 1" w.g. (0.25 kPa)
  Rated cfm: 2150 (60.9 cubic meters per minute)
 Pressure Indicator: ALNOR MicroManometer (digital micromanometer)
  Model: AXD 550
  Instrument I.D.: 66303
  Calibrated: Jun. 26, 2003
  Calibration Due: Jun. 26, 2004
 Leak Detection Equipment: ATI Analog Photometer
  Model: TDA-2E
  Ser. No.: 8462
  Calibrated: Oct. 31, 2003
  Calibration Due: Oct. 31, 2004
 Aerosol Generators:
  ATI Thermal Generator
   Model: TDA-5B
   Ser. No.: 15769
  ATI Laskin Nozzle Generator
   Model: TDA-4BL
   Ser. No.: 14718

TABLE 1

| Parameter | Result |
| --- | --- |
| AFS dP: | 0.452 |
| System Flowrate | ~2000 cfm (56.6 cubic |

TABLE 1-continued

| Parameter | Result |
| --- | --- |
|  | meters per minute) |
| Aerosol Type | Thermal PAO |
| Upstream Aerosol Concentration | 40 µg/l |
| Photometer Scale Setting | 0.1% |
| Approximate Manual Scan Speed | ~1 in/sec (25.4 mm/sec) |
| "Hole A" | Leak Detected** |
| "Hole B" | Leak Detected** |
| Background Concentration* | 0.04% |

*The "background concentration" was constantly present and attributed to the so-called "Bleed Through" phenomena. Essentially, it's a result of using thermally generated aerosol (with a particle diameter near the most penetrating particle size (MPPS), or 0.12 µm) for the challenge and operating the filter at such a high flowrate. The IEST recommendations were developed forsystems operating at approximately 90 feet per minute (fpm) (27.4 meters per minute) superficial velocity. In this test, the superficial media velocity is approximately 160 fpm (48.8 meters per minute). Furthermore, per IEST-RP-CC034.1, a Laskin nozzle generator (generating particles in the range of 0.6-0.7 µm diameter) is recommended for challenging this type of filter.
**IEST-RP-CC034.1 specifies a maximum penetration of 0.01%. It was not possible to base the presence of a leak on that penetration since the "background concentration" was higher than 0.01%. However, when the probe passed over the leaks, the photometer registered penetrations exceeding 0.1%, obviously indicating that leaks were present.

After scan testing was completed using an upstream challenge of approximately 40 µg/l, the output to the aerosol generated was adjusted to approximately 10 µg/l, and the filter was scanned again. That test yielded the same results as the test conducted at 40 µg/l. In order to be consistent with recommendations of IEST-RP-CC0034.1, testing was conducted using an ATI TDA-4BL Laskin Nozzle Generator. The results of that test are shown in Table 2.

TABLE 2

| Parameter | Result |
| --- | --- |
| AFS dP: | 0.452 |
| System Flowrate | ~2000 cfm (56.6 cubic meters per minute) |
| Aerosol Type | Cold PAO |
| Upstream Aerosol Concentration | 12 µg/l |
| Photometer Scale Setting | 0.01% |
| Approximate Manual Scan Speed | ~1 in/sec (25.4 mm/sec) |
| "Hole A" | Leak Detected** |
| "Hole B" | Leak Detected** |
| Background Concentration | n/a |

The "background concentration" due to bleed-through was not a problem when testing with the Laskin Nozzle generator. "Hole A" and "Hole B" were easily detected. Thus, due to "bleed through" effects, there is a background concentration present during testing using thermally generated PAO, which exceeds the maximum allowable penetration as recommended by IEST-RP-CC0034.1. This may be overcome by using a higher efficiency filter, such as an ULPA filter, which is designed to be highly efficient in removing 0.12 µm particles. The down side of this is the increase in pressure drop and increase in cost. As designed, the probe is effective in locating small pinhole leaks in the filter, with the filter operating at design flowrates and challenged with cold PAO generated with a Laskin Nozzle generator.

Procedure—Above Slot Style Probe

In another embodiment, the probe such as the probes 700, 1200 was utilized to scan test a Filtra 2000™. The probe was used to scan the opening between the Vee's on the downstream side of the V-bed filter without penetrating between the Vee's. The probe height was designed so that it extended beyond the media pack and overlapped the channel on each side of the Vee. For the test data provided below, the opening of the inlet sample port 1206 is 5.406 inches high×0.125 inches wide (137 mm×3.18 mm).

Design of the probe was confirmed as effective in locating leaks using a Filtra 2000™ was installed in a test rig and challenged with PAO. The filter was automatically scanned with the probe assembly that was coupled to a lead screw assembly which was rotated by a small servo motor. This allowed for precise control of the rotational speed of the motor and therefore accurate and precise control of the linear speed of the probe assembly. The testing is detailed below.

Two holes were intentionally placed in a Filtra 2000 using capillary tubes with an internal diameter (I.D.) of 0.020". "Hole 1" was created in the media pack on the downstream side of the filter, on the downstream side of the media pack, at a location approximately 6" from the side of filter. "Hole 2" was created in the media pack on the upstream side of the filter, on the upstream side of the media pack, at a location approximately 1" from the side of the filter. Holes were created in those locations because they represent locations where leaks are generally difficult to detect.

The variable frequency drive on the test rig was adjusted until the flowrate was approximately 2,400 cfm. An ATI TDA-4B Lite aerosol generator was used to generate PAO aerosol that was injected through the aerosol injection ring in the containment housing. The autoscan control and sampling system was used to conduct leak testing using a Lighthouse Solair 3100+ laser particle counter on the 0.3 micron size range. Results are provided in the Table below.

TABLE 3

Test Results Operating at 0.25 inches/sec Scan Speed

| Parameter | Result |
| --- | --- |
| System Flowrate | 2,400 cfm (70 meters per minute) |
| Aerosol Type | Cold PAO |
| Upstream Aerosol Concentration | 460,000,000 particles per cubic foot (13,025,750 particles per cubic meter) (0.3 micron diameter) |
| Scan Speed | 0.25 in/sec (.64 cm/sec) |
| "Hole 1" | Leak not detected |
| "Hole 2" | Leak not detected |

TABLE 4

Test Results Operating at 0.125 inches/sec Scan Speed

| Parameter | Result |
| --- | --- |
| System Flowrate | 2,400 cfm (70 meters per minute) |
| Aerosol Type | Cold PAO |
| Upstream Aerosol Concentration | 460,000,000 particles per cubic foot (13,025,750 particles per cubic meter) (0.3 micron diameter) |
| Scan Speed | 0.125 in/sec (0.32 cm/sec) |
| "Hole 1" | Leak detected @ 6.6" with 0.014" penetration |
| "Hole 2" | Threshold leak detected with 0.9" of 0.008% penetration |

As designed, at rated airflow of 2,400 cfm and an upstream challenge concentration of 460,000,000 particles per cubic foot of 0.3 micron diameter, the system was capable of locating pinhole leaks at a scan speed of 0.125 inches/sec, but not 0.250 inches/sec. Using higher aerosol challenge upstream may allow leaks to be located at faster scan speeds, since the amount of challenge coming through the leak would be higher and detected more easily. Also, at lower airflows the system is capable of finding leaks at faster scan speeds since the particles passing through the pinhole are not diluted downstream of the filter by clean air and are thus more easily detected during scanning.

Scan speeds of up to about 0.1875 inches/sec (0.48 cm/sec) have demonstrated to produce acceptable scanning results. Thus, in systems having an operational velocity of less than or equal to 2400 cubic feet per minute, a scan speed of less than or equal to about 0.1875 inches per second may be utilized to detect leaks in v-bank filters wherein the upstream challenge is about 300,000,000 particles per cubic foot (about 8,495,050 particles per cubic meters) in a 2,400 cfm flow. It is contemplated that the scan rate may rise at lower operational velocities and/or at higher challenges.

Thus, a method and apparatus has been provided that enables scan testing of v-bank filters. Advantageously, the invention will allow the use of v-bank filters in applications where testing for pin-hole leaks is required.

Although various embodiments which incorporate the teachings of the present invention have been shown and described in detail herein, those skilled in the art can readily devise many other varied embodiment that still incorporate these teachings.

What is claimed is:

1. A method for testing a v-bank filter, comprising:
    providing a challenge to a v-bank filter having at least two adjacent banks of filter media arranged in a "v" configuration;
    scanning a probe across a first opening defined between the adjacent banks of filter media;
    sampling air passing through the banks of filter media and into the probe; and
    determining if a sample is indicative of a leak.

2. The method of claim 1, wherein scanning further comprises:
    moving a first sample port formed in a body of the probe across the first opening; and
    moving a second sample port formed in the body of the probe across a second opening defined adjacent the first opening.

3. The method of claim 1, wherein scanning further comprises:
    moving the probe at a speed of less than 0.1875 inches per second (0.48 cm/sec).

4. The method of claim 1, wherein scanning further comprises:
    moving the probe at a speed of less than 0.125 inches per second (0.32 cm/sec).

5. The method of claim 1, wherein scanning further comprises:
    engaging a guide of the probe with the filter.

6. The method of claim 1, further comprising:
    extending a body of the probe into the first opening between the adjacent banks of filter media prior to scanning the probe across the first opening.

7. The method of claim 6, wherein sampling air passing through the banks of filter media comprises drawing samples from facing banks of the filter media.

8. The method of claim 7, wherein sampling air passing through the banks of filter media further comprises drawing samples into the probe from multiple apertures, wherein an orifice of an aperture furthest from a test instrument is greater than an orifice of an aperture closest to the test instrument.

9. The method of claim 1, wherein scanning the probe across the first opening comprises aligning the probe to the v-bank filter with one or more guides.

10. The method of claim 9, wherein scanning the probe across the first opening further comprises moving the probe by a lead screw coupled to a servo motor and controlling the rotational speed of the servo motor.

11. A method for testing a v-bank filter, comprising:
    providing a challenge to a v-bank filter having at least two adjacent banks of filter media arranged in a "v" configuration;
    scanning a probe across an opening defined between the adjacent banks of filter media;
    sampling air passing through the banks of filter media and into the probe; determining if a sample is indicative of a leak; and
    challenging the filter with at least 300,000,000 particles per cubic foot (8,495,050 particles per cubic meters).

12. The method of claim 11, wherein scanning further comprises:
    providing at least 2000 cfm (56.6 cubic meters per minute) of air flow through the filter.

13. The method of claim 11, wherein scanning further comprises:
    moving a first sample port formed in a body of the probe across the first opening; and
    moving a second sample port formed in the body of the probe across a second opening defined adjacent the first opening.

14. The method of claim 11, wherein scanning further comprises:
    moving the probe at a speed of less than 0.1875 inches per second (0.48 cm/sec).

15. The method of claim 11, wherein scanning further comprises:
    moving the probe at a speed of less than 0.125 inches per second (0.32 cm/sec).

16. The method of claim 11, wherein scanning further comprises:
    engaging a guide of the probe with the filter.

17. The method of claim 11, wherein sampling air passing through the banks of filter media further comprises drawing samples into the probe from multiple apertures, wherein an orifice of an aperture furthest from a test instrument is greater than an orifice of an aperture closest to the test instrument.

18. The method of claim 11, wherein scanning the probe across the first opening comprises aligning the probe to the v-bank filter with one or more guides.

19. A method for testing a v-bank filter, comprising:
    providing a challenge to a v-bank filter having at least two adjacent banks of filter media arranged in a "v" configuration;
    scanning a probe across an opening defined between the adjacent banks of filter media;
    sampling air passing through the banks of filter media and into the probe; determining if a sample is indicative of a leak; and
    providing at least 2000 cfm (56.6 cubic meters per minute) of air flow through the filter.

* * * * *